United States Patent
Finn et al.

(10) Patent No.: US 10,488,371 B1
(45) Date of Patent: Nov. 26, 2019

(54) NONDESTRUCTIVE INSPECTION USING THERMOACOUSTIC IMAGERY AND METHOD THEREFOR

(71) Applicant: United Technologies Corporation, Farmington, CT (US)

(72) Inventors: Alan Matthew Finn, Hebron, CT (US); Amit Surana, West Hartford, CT (US); Matthew O. Williams, Honolulu, HI (US); Edgar A. Bernal, Webster, NY (US); Ozgur Erdinc, Mansfield, CT (US)

(73) Assignee: United Technologies Corporation, Farmington, CT (US)

( * ) Notice: Subject to any disclaimer, the term of this patent is extended or adjusted under 35 U.S.C. 154(b) by 0 days.

(21) Appl. No.: 15/971,254

(22) Filed: May 4, 2018

(51) Int. Cl.
   *G06K 9/00* (2006.01)
   *G01N 3/02* (2006.01)
   (Continued)

(52) U.S. Cl.
   CPC .......... *G01N 29/348* (2013.01); *G01N 21/71* (2013.01); *G01N 25/72* (2013.01); *G01N 29/228* (2013.01);
   (Continued)

(58) Field of Classification Search
   CPC ...... G01N 25/72; G01N 29/043; G01N 29/12; G01N 15/1475; G01N 2015/1445; G01N 21/31; G01N 21/51; G01N 2291/0289; G01N 2291/102; G01N 2291/105; G01N 29/4445; G01N 21/00; G01N 29/11; G01N 29/30; G01N 2223/6466; G01N 2291/0258; G01N 25/00; G01N 29/00; G01N 29/041; G01N 29/226; G01N 29/348; G01N 21/1702; G01N 29/14; G01N 29/221; G01N 29/2431; G01N 29/34; G01N 29/343;
   (Continued)

(56) References Cited

U.S. PATENT DOCUMENTS

| 3,804,397 A | 4/1974 | Neumann |
| 4,402,053 A | 8/1983 | Kelley et al. |

(Continued)

FOREIGN PATENT DOCUMENTS

| CA | 2820732 A1 | 12/2014 |
| DE | 19710743 A1 | 9/1998 |

(Continued)

OTHER PUBLICATIONS

Blachnio et al, "Assessment of Technical Condition Demonstrated by Gas Turbine Blades by Processing of Images of Their Surfaces", Journal of KONBiN, 1(21), 2012, pp. 41-50.

(Continued)

*Primary Examiner* — Taeho Jo
(74) *Attorney, Agent, or Firm* — Bachman & LaPointe, P.C.

(57) ABSTRACT

A method for nondestructive vibrothermography inspection of a component, the method includes generating ultrasonic excitations in a component over a range of frequencies; determining a thermal signature in the component from the excitations; registering a model with the thermal signature; determining damage based on the thermal signal and model; and classifying the component based on the determining.

19 Claims, 4 Drawing Sheets

(51) Int. Cl.
G01N 27/20 (2006.01)
G01N 25/72 (2006.01)
G01N 29/34 (2006.01)
G01N 29/22 (2006.01)
G06T 7/00 (2017.01)
G01N 21/71 (2006.01)
G01N 29/46 (2006.01)

(52) U.S. Cl.
CPC ............ *G01N 29/46* (2013.01); *G06T 7/0004* (2013.01); *G01N 2291/2693* (2013.01)

(58) Field of Classification Search
CPC .. G01N 29/4409; G01N 21/71; G01N 29/228; G01N 29/46; G01N 2291/2693; G06T 7/0004
USPC ...................................................... 250/341.6
See application file for complete search history.

(56) References Cited

U.S. PATENT DOCUMENTS

| | | |
|---|---|---|
| 4,403,294 A | 9/1983 | Hamada et al. |
| 4,873,651 A | 10/1989 | Raviv |
| 5,064,291 A | 11/1991 | Reiser |
| 5,119,678 A | 6/1992 | Bashyam et al. |
| 5,345,514 A | 9/1994 | Mandavieh et al. |
| 5,345,515 A | 9/1994 | Nishi et al. |
| 5,351,078 A | 9/1994 | Lemelson |
| 5,963,328 A | 10/1999 | Yoshida et al. |
| 6,153,889 A | 11/2000 | Jones |
| 6,177,682 B1 | 1/2001 | Bartulovic et al. |
| 6,399,948 B1* | 6/2002 | Thomas ................ G01N 25/72 250/334 |
| 6,434,267 B1 | 8/2002 | Smith |
| 6,462,813 B1 | 10/2002 | Haven et al. |
| 6,759,659 B2 | 7/2004 | Thomas et al. |
| 6,804,622 B2 | 10/2004 | Bunker et al. |
| 6,907,358 B2 | 6/2005 | Suh et al. |
| 6,965,120 B1 | 11/2005 | Beyerer et al. |
| 7,026,811 B2 | 4/2006 | Roney, Jr. et al. |
| 7,064,330 B2 | 6/2006 | Raulerson et al. |
| 7,119,338 B2 | 10/2006 | Thompson et al. |
| 7,122,801 B2 | 10/2006 | Favro et al. |
| 7,164,146 B2 | 1/2007 | Weir et al. |
| 7,190,162 B2 | 3/2007 | Tenley et al. |
| 7,233,867 B2 | 6/2007 | Pisupati et al. |
| 7,240,556 B2 | 7/2007 | Georgeson et al. |
| 7,272,529 B2 | 9/2007 | Hogan et al. |
| 7,313,961 B2 | 1/2008 | Tenley et al. |
| 7,415,882 B2 | 8/2008 | Fetzer et al. |
| 7,446,886 B2 | 11/2008 | Aufmuth et al. |
| 7,489,811 B2 | 2/2009 | Brummel et al. |
| 7,602,963 B2 | 10/2009 | Nightingale et al. |
| 7,689,030 B2 | 3/2010 | Suh et al. |
| 7,724,925 B2 | 5/2010 | Shepard |
| 7,738,725 B2 | 6/2010 | Raskar et al. |
| 7,823,451 B2 | 11/2010 | Sarr |
| 7,966,883 B2 | 6/2011 | Lorraine et al. |
| 8,204,294 B2 | 6/2012 | Alloo et al. |
| 8,208,711 B2 | 6/2012 | Venkatachalam et al. |
| 8,221,825 B2 | 7/2012 | Reitz et al. |
| 8,239,424 B2 | 8/2012 | Haigh et al. |
| 8,431,917 B2 | 4/2013 | Wang et al. |
| 8,449,176 B2 | 5/2013 | Shepard |
| 8,520,931 B2 | 8/2013 | Tateno |
| 8,528,317 B2 | 9/2013 | Gerez et al. |
| 8,692,887 B2 | 4/2014 | Ringermacher et al. |
| 8,744,166 B2 | 6/2014 | Scheid et al. |
| 8,761,490 B2 | 6/2014 | Scheid et al. |
| 8,781,209 B2 | 7/2014 | Scheid et al. |
| 8,781,210 B2 | 7/2014 | Scheid et al. |
| 8,792,705 B2 | 7/2014 | Scheid et al. |
| 8,913,825 B2 | 12/2014 | Taguchi et al. |
| 8,983,794 B1* | 3/2015 | Motzer ................ G01B 17/06 702/150 |
| 9,037,381 B2 | 5/2015 | Care |
| 9,046,497 B2 | 6/2015 | Kush et al. |
| 9,080,453 B2 | 7/2015 | Shepard et al. |
| 9,116,071 B2 | 8/2015 | Hatcher, Jr. et al. |
| 9,134,280 B2 | 9/2015 | Cataldo et al. |
| 9,146,205 B2 | 9/2015 | Renshaw et al. |
| 9,151,698 B2 | 10/2015 | Jahnke et al. |
| 9,154,743 B2 | 10/2015 | Hatcher, Jr. et al. |
| 9,251,582 B2 | 2/2016 | Lim et al. |
| 9,300,865 B2 | 3/2016 | Wang et al. |
| 9,305,345 B2 | 4/2016 | Lim et al. |
| 9,458,735 B1 | 10/2016 | Diwinsky et al. |
| 9,465,385 B2 | 10/2016 | Kamioka et al. |
| 9,467,628 B2 | 10/2016 | Geng et al. |
| 9,471,057 B2 | 10/2016 | Scheid et al. |
| 9,476,798 B2 | 10/2016 | Pandey et al. |
| 9,476,842 B2 | 10/2016 | Drescher et al. |
| 9,483,820 B2 | 11/2016 | Lim et al. |
| 9,488,592 B1* | 11/2016 | Maresca ............ G01N 21/8851 |
| 9,519,844 B1 | 12/2016 | Thompson et al. |
| 9,562,870 B2* | 2/2017 | Bouteyre ................ F03D 1/065 |
| 9,594,059 B1 | 3/2017 | Brady et al. |
| 9,734,568 B2 | 5/2017 | Vajaria et al. |
| 9,785,919 B2 | 10/2017 | Diwinsky et al. |
| 9,804,997 B2 | 10/2017 | Sharp et al. |
| 9,808,933 B2 | 11/2017 | Lin et al. |
| 2002/0121602 A1* | 9/2002 | Thomas ................ G01N 25/72 250/341.6 |
| 2002/0167660 A1 | 11/2002 | Zaslavsky |
| 2003/0117395 A1 | 6/2003 | Yoon |
| 2003/0205671 A1* | 11/2003 | Thomas ................ G01N 25/72 250/341.6 |
| 2004/0089811 A1* | 5/2004 | Lewis ................ G01N 25/72 250/341.6 |
| 2004/0089812 A1* | 5/2004 | Favro ................ G01N 3/60 250/341.6 |
| 2004/0139805 A1* | 7/2004 | Antonelli ................ B23K 31/12 73/799 |
| 2004/0201672 A1 | 10/2004 | Varadarajan et al. |
| 2004/0240600 A1* | 12/2004 | Freyer ................ G01M 15/14 376/159 |
| 2004/0245469 A1* | 12/2004 | Favro ................ G01N 25/72 250/341.6 |
| 2004/0247170 A1 | 12/2004 | Furze et al. |
| 2005/0008215 A1* | 1/2005 | Shepard ................ G01N 25/72 382/141 |
| 2005/0151083 A1* | 7/2005 | Favro ................ G01N 3/60 250/341.6 |
| 2005/0167596 A1* | 8/2005 | Rothenfusser ............ G01N 3/60 250/341.6 |
| 2007/0017297 A1* | 1/2007 | Georgeson ............ G01M 5/0016 73/801 |
| 2007/0045544 A1* | 3/2007 | Favro ................ G01N 3/60 250/341.6 |
| 2008/0022775 A1* | 1/2008 | Sathish ................ G01N 25/72 73/606 |
| 2008/0053234 A1* | 3/2008 | Staroselsky ............ G01N 25/72 73/649 |
| 2008/0183402 A1* | 7/2008 | Malkin ................ G06F 17/5018 702/34 |
| 2008/0229834 A1* | 9/2008 | Bossi ................ G01N 29/11 73/627 |
| 2008/0247635 A1* | 10/2008 | Davis ................ G06T 19/00 382/152 |
| 2008/0247636 A1* | 10/2008 | Davis ................ G06T 19/00 382/152 |
| 2009/0000382 A1* | 1/2009 | Sathish ................ G01N 25/72 73/606 |
| 2009/0010507 A1 | 1/2009 | Geng |
| 2009/0066939 A1 | 3/2009 | Venkatachalam et al. |
| 2009/0128643 A1 | 5/2009 | Kondo et al. |
| 2009/0252987 A1 | 10/2009 | Greene, Jr. |
| 2009/0279772 A1* | 11/2009 | Sun ................ G06K 9/6298 382/141 |
| 2009/0312956 A1* | 12/2009 | Zombo ................ F01D 5/288 702/34 |

(56) References Cited

U.S. PATENT DOCUMENTS

| | | | |
|---|---|---|---|
| 2011/0062339 A1* | 3/2011 | Ruhge | G01N 25/72 250/340 |
| 2012/0154599 A1 | 6/2012 | Huang | |
| 2012/0275667 A1 | 11/2012 | Lu | |
| 2012/0293647 A1 | 11/2012 | Singh et al. | |
| 2013/0028478 A1* | 1/2013 | St-Pierre | G01B 11/002 382/103 |
| 2013/0070897 A1 | 3/2013 | Jacotin | |
| 2013/0235897 A1* | 9/2013 | Bouteyre | F03D 1/065 374/4 |
| 2013/0250067 A1 | 9/2013 | Laxhuber et al. | |
| 2014/0022357 A1 | 1/2014 | Yu et al. | |
| 2014/0056507 A1* | 2/2014 | Doyle | G01B 11/002 382/152 |
| 2014/0098836 A1 | 4/2014 | Bird | |
| 2014/0184786 A1* | 7/2014 | Georgeson | G01N 21/8851 348/128 |
| 2014/0198185 A1 | 7/2014 | Haugen et al. | |
| 2014/0200832 A1* | 7/2014 | Troy | G01N 29/043 702/38 |
| 2015/0041654 A1* | 2/2015 | Barychev | G01N 21/3581 250/338.4 |
| 2015/0046098 A1* | 2/2015 | Jack | G06F 17/5009 702/33 |
| 2015/0086083 A1 | 3/2015 | Chaudhry et al. | |
| 2015/0128709 A1* | 5/2015 | Stewart | G01N 29/11 73/588 |
| 2015/0138342 A1 | 5/2015 | Brdar et al. | |
| 2015/0185128 A1* | 7/2015 | Chang | G01M 5/0091 702/35 |
| 2015/0253266 A1 | 9/2015 | Lucon et al. | |
| 2016/0012588 A1 | 1/2016 | Taguchi et al. | |
| 2016/0043008 A1* | 2/2016 | Murray | G01N 29/2418 438/5 |
| 2016/0109283 A1* | 4/2016 | Broussais-Colella | G01N 29/11 73/579 |
| 2016/0178532 A1 | 6/2016 | Lim et al. | |
| 2016/0241793 A1 | 8/2016 | Ravirala et al. | |
| 2016/0314571 A1 | 10/2016 | Finn et al. | |
| 2016/0328835 A1* | 11/2016 | Maresca, Jr. | G01N 21/8851 |
| 2017/0011503 A1* | 1/2017 | Newman | G01N 25/72 |
| 2017/0023505 A1* | 1/2017 | Maione | G01B 21/18 |
| 2017/0052152 A1 | 2/2017 | Tat et al. | |
| 2017/0085760 A1 | 3/2017 | Ernst et al. | |
| 2017/0090458 A1 | 3/2017 | Lim et al. | |
| 2017/0122123 A1 | 5/2017 | Kell et al. | |
| 2017/0184469 A1* | 6/2017 | Chang | G01M 5/0091 |
| 2017/0184549 A1 | 6/2017 | Reed et al. | |
| 2017/0184650 A1* | 6/2017 | Chang | G01M 5/0091 |
| 2017/0221274 A1 | 8/2017 | Chen et al. | |
| 2017/0234837 A1* | 8/2017 | Hall | B06B 3/00 73/602 |
| 2017/0258391 A1 | 9/2017 | Finn et al. | |
| 2017/0262965 A1 | 9/2017 | Kiong et al. | |
| 2017/0262977 A1 | 9/2017 | Finn et al. | |
| 2017/0262979 A1 | 9/2017 | Kiong et al. | |
| 2017/0262985 A1 | 9/2017 | Finn et al. | |
| 2017/0262986 A1 | 9/2017 | Kiong et al. | |
| 2017/0270651 A1 | 9/2017 | Bailey et al. | |
| 2017/0297095 A1* | 10/2017 | Zalameda | B22D 23/003 |
| 2018/0002039 A1 | 1/2018 | Finn et al. | |
| 2018/0005362 A1 | 1/2018 | Wang et al. | |
| 2018/0019097 A1 | 1/2018 | Harada et al. | |
| 2018/0098000 A1 | 4/2018 | Park et al. | |
| 2018/0111239 A1 | 4/2018 | Zak et al. | |

FOREIGN PATENT DOCUMENTS

| | | |
|---|---|---|
| EP | 1961919 A2 | 8/2008 |
| GB | 2545271 A | 6/2017 |
| JP | 2015161247 A | 9/2015 |
| SG | 191452 A1 | 7/2013 |
| WO | 2016112018 A1 | 7/2016 |
| WO | 2016123508 A1 | 8/2016 |
| WO | 2016176524 A1 | 11/2016 |

OTHER PUBLICATIONS

Raskar et al., 'A Non-photorealistic Camera: Depth Edge Detection and Stylized Rendering using Multi-flash Imaging' ACM Transactions on Graphics, 2004 http://www.merl.com/publications/docs/TR2006-107.pdf.

Feris et al., 'Specular Reflection Reduction with Multi-Flash Imaging', 17th Brazilian Symposium on Computer Graphics and Image Processing, 2004. http://rogerioferis.com/publications/FerisSIB04.pdf.

Holland, "First Measurements from a New Broadband Vibrothermography Measurement System", AIP Conference Proceedings, 894 (2007), pp. 478-483. http://link.aip.org/link/doi/10.106311.27180101 \.

Gao et al., 'Detecting Cracks in Aircraft Engine Fan Blades Using Vibrothermography Nondestructive Evaluation', RESS Special Issue on Accelerated Testing, 2014, http://dx.doi.org/10.1016/j.ress.2014.05.009.

Holland, 'Thermographic Signal Reconstruction for Vibrothermography', Infrared Physics & Technology 54 (2011) 503-511.

M. Sznaier, O. Camps, N. Ozay, T. Ding, G. Tadmor and D. Brooks, "The Role of Dynamics in Extracting Information Sparsely Encoded in High Dimensional Data Streams", in Dynamics of Information Systems, Hirsch, M.J.; Pardalos, P.M.; Murphey, R. (Eds.), pp. 1-28, Springer Verlag, 2010.

M. Fazel, H. Hindi, and S. Boyd, "A Rank Minimization Heuristic with Application to Minimum Order System Approximation", American Control Conference, Arlington, Virginia, pp. 4734-4739, Jun. 2001.

Meola et al., 'An Excursus on Infrared Thermography Imaging', J. Imaging 2016, 2, 36 http://www.mdpi.com/2313-433X/2/4/36/pdf.

Yu et al., 'ASIFT: An Algorithm for Fully Affine Invariant Comparison', Image Processing on Line on Feb. 24, 2011. http://www.ipol.im/pub/art/2011/my-asift/article.pdf.

Schemmel et al., 'Measurement of Direct Strain Optic Coefficient of YSZ Thermal Barrier Coatings at Ghz Frequencies', Optics Express, v.25, n.17, Aug. 21, 2017, https://doi.org/10.1364/OE.25.019968.

Jean-Yves Bouguet, "Camera Calibration Toolbox for Matlab", http://www.vision.caltech.edu/bouguetj/calib_doc/, accessed on Nov. 10, 2017.

Yu et al. 'Shadow Graphs and 3D Texture Reconstruction', IJCV, vol. 62, No. 1-2, 2005, pp. 35-60.

Gao et al., 'A Statistical Method for Crack Detection from Vibrothermography Inspection Data',(2010) Statistics Preprints. Paper 68. http://lib.dr.iastate.edu/stat_las_preprints/68.

Li1 Ming; Holland1 Stephen D.; and Meeker1 William Q.1 "Statistical Methods for Automatic Crack Detection Based on Vibrothermography Sequence-of-Images Data" (2010). Statistics Preprints. 69.

Henneke et al. 'Detection of Damage in Composite Materials by Vibrothermography', ASTM special technical publication (696), American Society for Testing and Materials, 1979, pp. 83-95.

http://www.npl.co.uk/commercial-services/sector-case-studies/thermal-imaging-reveals-the-invisible; Apr. 17, 2012.

Tian et al., 'A Statistical Framework for Improved Automatic Flaw Detection in Nondestructive Evaluation Images', Technometrics, 59, 247-261. Feb. 1, 2017.

Emmanuel J. Cand'es1,2, Xiaodong LI2, Yi MA3,4, and John Wright4, "Robust Principal Component Analysis", (1)Department of Statistics, Stanford University, Stanford, CA; (2)Department of Mathematics, Stanford University, Stanford, CA; (3, 4) Electrical and Computer Engineering, UIUC, Urbana, IL (4) Microsoft Research Asia, Beijing, China, Dec. 17, 2009.

Sebastien Parent; "From Human to Machine: How to Be Prepared for Integration of Automated Visual Inspection"Quality Magazine, https://www.qualitymag.com/articles/91976. Jul. 2, 2014.

(56) References Cited

OTHER PUBLICATIONS http://www.yxlon.com/products/x-ray-and-ct-inspection-systems/yxlon-mu56-tb, 2016.
U.S. Non-Final Office Action dated Mar. 5, 2019 for corresponding U.S. Appl. No. 15/971,227.
U.S. Non-Final Office Action dated Apr. 16, 2019 for corresponding U.S. Appl. No. 15/970,985.
U.S. Non-Final Office Action dated May 28, 2019 for corresponding U.S. Appl. No. 15/971,214.

* cited by examiner

NONDESTRUCTIVE INSPECTION USING THERMOACOUSTIC IMAGERY AND METHOD THEREFOR

BACKGROUND

The present disclosure relates to nondestructive component inspection and, more particularly, to a nondestructive thermoacoustic imagery system for prognostics and health management, preventative maintenance, and repair of gas turbine engine parts.

Manufactured components may incur defects or imperfections during manufacturing or suffer wear and defect during operation. These components, therefore, are episodically or periodically inspected. Some types of defects consist of delamination or improper bonding of composite structures. These types of defects may be detected by thermoacoustic techniques (also known as vibroacoustic, vibrothermography, thermosonic, or sonic infrared techniques) wherein vibration of the component induces localized heating at defect locations. The heating is detected by an infrared camera. Typically, the imagery is reviewed manually for the detection of defects. These reviews are tedious, time consuming, imprecise, and may be error prone.

More recently, automated statistical analysis has been performed for crack detection using rapid exterior heating of a component and infrared imaging. For instance, pulsed thermography, where a very short intense flash of light heats a component, has been used to show thermal conductivity of a coating. These methods, however, require external heating of the component, which may not be applicable to composite material components.

SUMMARY

A method for nondestructive vibrothermography inspection of a component, the method according to one disclosed non-limiting embodiment of the present disclosure includes generating ultrasonic excitations in a component over a range of frequencies; determining a thermal signature in the component from the excitations; comparing the thermal signature with a model of the component; and classifying the component based on the comparing.

A further embodiment may additionally and/or alternatively include classifying the component comprises identifying whether the component is acceptable or unacceptable.

A further embodiment may additionally and/or alternatively include wherein classifying the component comprises identifying a disbond area.

A further aspect of the present disclosure includes, wherein classifying the component comprises identifying a disbond area only within a predetermined area.

A further embodiment may additionally and/or alternatively include the predetermined area is an area that includes a rigid internal structure.

A further embodiment may additionally and/or alternatively include that the predetermined area is adjacent the rigid internal structure and a cover.

A further embodiment may additionally and/or alternatively include the predetermined area is adjacent to a non-rigid internal structure and a cover.

A further embodiment may additionally and/or alternatively include damping the component within a fixture.

A further embodiment may additionally and/or alternatively include wherein the range of frequencies comprises frequencies from 20 kHz to 2 MHz.

A further embodiment may additionally and/or alternatively include wherein the thermal signature is from 0.5 to 22 µm in wavelength.

A method for nondestructive vibrothermography inspection of a component, the method according to one disclosed non-limiting embodiment of the present disclosure includes generating ultrasonic excitations in a component over a range of frequencies; determining a thermal signature in the component from the excitations; comparing the thermal signature with a model of the component; identifying a defect within a predetermined area designated by the model; and classifying the component based on the identifying.

A further embodiment may additionally and/or alternatively include that the predetermined area is an area that includes a rigid internal structure.

A further embodiment may additionally and/or alternatively include that the predetermined area is adjacent the rigid internal structure and a cover.

A further embodiment may additionally and/or alternatively include that the predetermined area is adjacent to a non-rigid internal structure and a cover.

A further embodiment may additionally and/or alternatively include orienting the model with respect to the component based on an edge of the model and an edge of the component.

A further embodiment may additionally and/or alternatively include that the model is at least one of an as-designed model, an as-built model, a previous condition model, and a model derived from a thermal signature.

A nondestructive vibrothermography inspection system to inspect a component, the system according to one disclosed non-limiting embodiment of the present disclosure includes a fixture to retain a component; an ultrasonic excitation source directed toward the component to generate ultrasonic excitations in the component over a range of frequencies; a thermography system directed toward the component to determine a thermal signature in the component from the excitations; and a controller operable to classify a portion of the component as a defect based on a comparison between the thermal signature of the component and a model of the component.

A further embodiment may additionally and/or alternatively include that the a database with the model of the component that identifies a location of an internal structure of the component.

A further embodiment may additionally and/or alternatively include that the controller will only classify a portion of the component as the defect if the defect is adjacent to the internal structure.

A further embodiment may additionally and/or alternatively include that the model is at least one of an as-designed model, an as-built model, a previous condition model, and a model derived from a thermal signature.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

BRIEF DESCRIPTION OF THE DRAWINGS

Various features will become apparent to those skilled in the art from the following detailed description of the disclosed non-limiting embodiments. The drawings that accompany the detailed description can be briefly described as follows.

DETAILED DESCRIPTION

Figure 1:
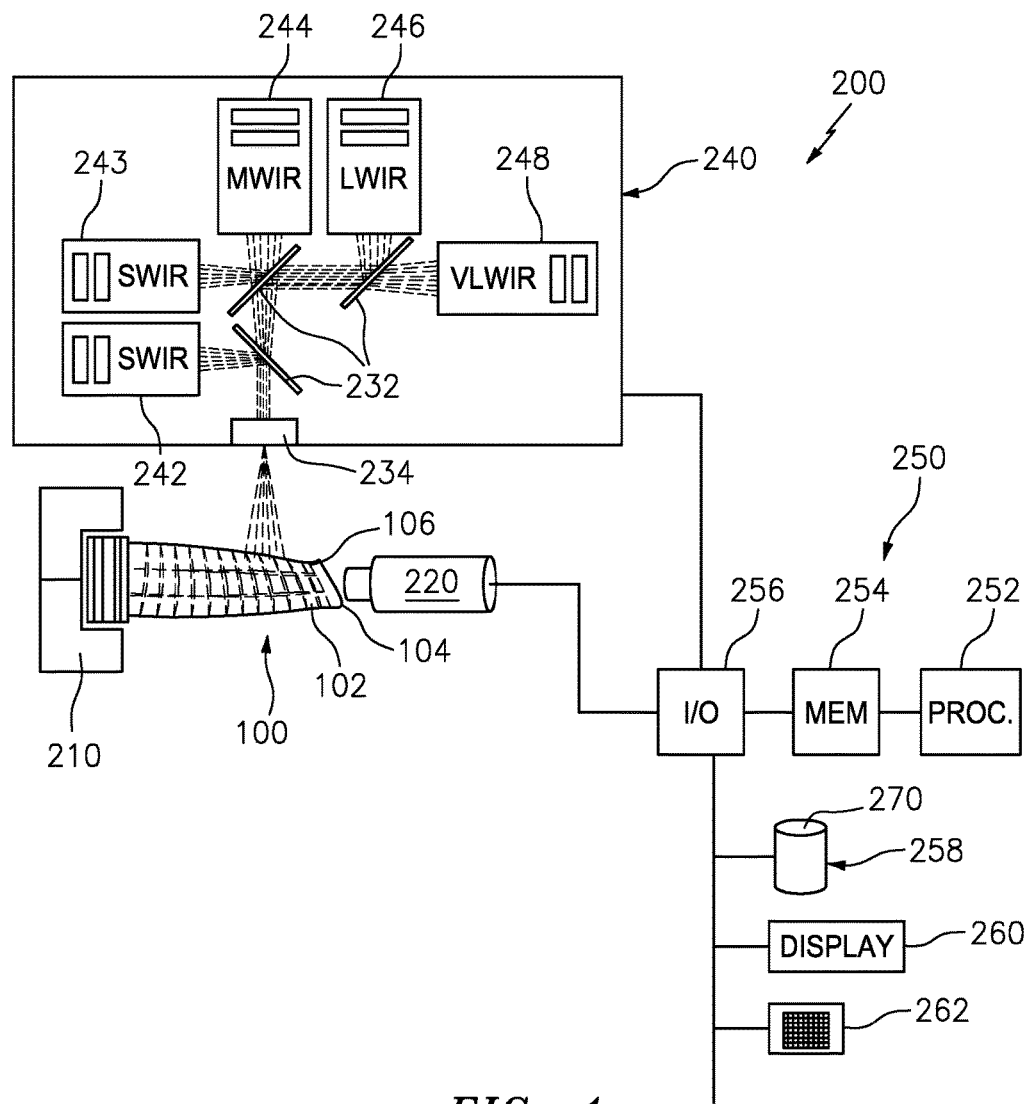
FIG. 1 is a schematic view of a nondestructive thermoacoustic imagery system.

FIG. 1 schematically illustrates a nondestructive thermoacoustic imagery system 200 particularly applicable to composite material manufacturing defects such as disbonding or delamination. An example component 100, for example a fan blade of a gas turbine engine, may have a substrate 102, a cover 104, and a rigid internal structure 106. In this example, the cover 104 is bonded to the internal structure 106 which, in turn, is either bonded to, or is an integral component of, the substrate 102. While this disclosure is taught with respect to a fan blade, it is explicitly contemplated that the teaching herein is applicable to both natural and manufactured composite objects with internal structure.

The nondestructive vibrothermography inspection system 200 includes a fixture 210 to retain the component 100, an ultrasonic excitation source 220, a thermography system 240, and a control system 250. The nondestructive thermoacoustic imagery system 200 utilizes models of the component internal structure 106 to guide the detection and classification of potential component defects. The ultrasonic excitation source 220 may be capable of generating a broad range of frequencies, for example, from 20 kHz up to 2 MHz. This causes localized heating from friction, principally at the edges of a defect in the component 100.

The thermography system 240, for example, includes one or more thermal sensors operable to obtain thermal radiation over a wide spectral range such as from 0.5 to 22 µm in wavelength. In one embodiment, the thermography system 240 may include one or more of a short-wave infrared (SWIR) module 242, a mid-wave infrared (MWIR) module 244, a long-wave infrared (LWIR) module 246, a very long-wave infrared (VLWIR) module 248, and a broadband infrared module (not shown) that optionally utilize beam splitters 232 to view a component such as an example blade 100 through a single lens 234 at multiple wavelengths simultaneously. Short-wave infrared (SWIR) refers to nonvisible light falling between 1400 and 3000 nanometers (nm) in wavelength. Mid-wave infrared (MWIR) is a subset of the infrared band of the electromagnetic spectrum, covering the wavelengths ranging from 3 µm to 5 µm (3000 nm to 5000 nm). Long-wave infrared (LWIR) is a subset of the infrared band of the electromagnetic spectrum, covering the wavelengths ranging from the wavelengths ranging from 8 µm to 14 µm (8000 nm to 14000 nm). Very long-wave infrared (VLWIR) is a subset of the infrared band of the electromagnetic spectrum, covering the wavelengths ranging from the wavelengths ranging from the 12 µm to 22 µm (12000 nm to 22000 nm). In alternative embodiments, parallel optical channels are used with bandpass filters to separate the multispectral bands. In yet another embodiment, a multispectral random imaging camera may be used.

The component 100 may be imaged by the thermography system 240 before, during, and after the ultrasonic excitation source 220 is activated. The sensing, in one embodiment, may occur at a rate significantly faster than the on/off cycle of the ultrasonic excitation source 220 such that multiple readings by the thermography system 240 are taken while the ultrasonic excitation source 220 is off, multiple readings are taken while the ultrasonic excitation source 220 is on, and yet more readings are taken while ultrasonic excitation source 220 is off again. The component 100 may be imaged in total, in part, or in a sequence covering some or all of the component while the ultrasonic excitation source 220 is successively turned off, on, and off for each location being imaged. If the component 100 is imaged in a sequence of overlapping locations, the multiple image sequences may be mapped to produce a single image sequence that covers a larger area of the component. The time history of each imaged location on the component may be analyzed.

The control system 250 includes at least one computing device that may include hardware, firmware, and/or software components that are configured to perform the functions disclosed herein, including the operation of the ultrasonic excitation source 220, and the thermography system 240. While not specifically shown, the control system 250 may include other computing devices (e.g., servers, mobile computing devices, etc.) and computer aided manufacturer (CAM) systems which may be in communication with each other and/or the control system 250 via a communication network to perform one or more of the disclosed functions.

The control system 250 may include at least one processor 252 (e.g., a controller, microprocessor, microcontroller, digital signal processor, etc.), memory 254, and an input/output (I/O) subsystem 256. The control system 250 may be embodied as any type of computing device (e.g., a workstation, an embedded computer, an FPGA, a tablet computer, smart phone, body-mounted device or wearable device, etc.), a server, an enterprise computer system, a network of computers, a combination of computers and other electronic devices, or other electronic devices. Although not specifically shown, the I/O subsystem 256 typically includes, for example, an I/O controller, a memory controller, and one or more I/O ports. The processor 252 and the I/O subsystem 256 are communicatively coupled to the memory 254. The memory 254 may be embodied as any type of computer memory device (e.g., volatile memory such as various forms of random access memory).

The I/O subsystem 256 may also be communicatively coupled to a number of hardware, firmware, and/or software components, including a data storage device 258, a display 260, and a user interface (UI) subsystem 262. The data storage device 258 may include one or more hard drives or other suitable persistent storage devices (e.g., flash memory, memory cards, memory sticks, and/or others). A database 270 for models of the component may reside at least temporarily in the data storage device 258 and/or other data storage devices (e.g., data storage devices that are "in the cloud" or otherwise connected to the control system 250 by a network).

Figure 2:
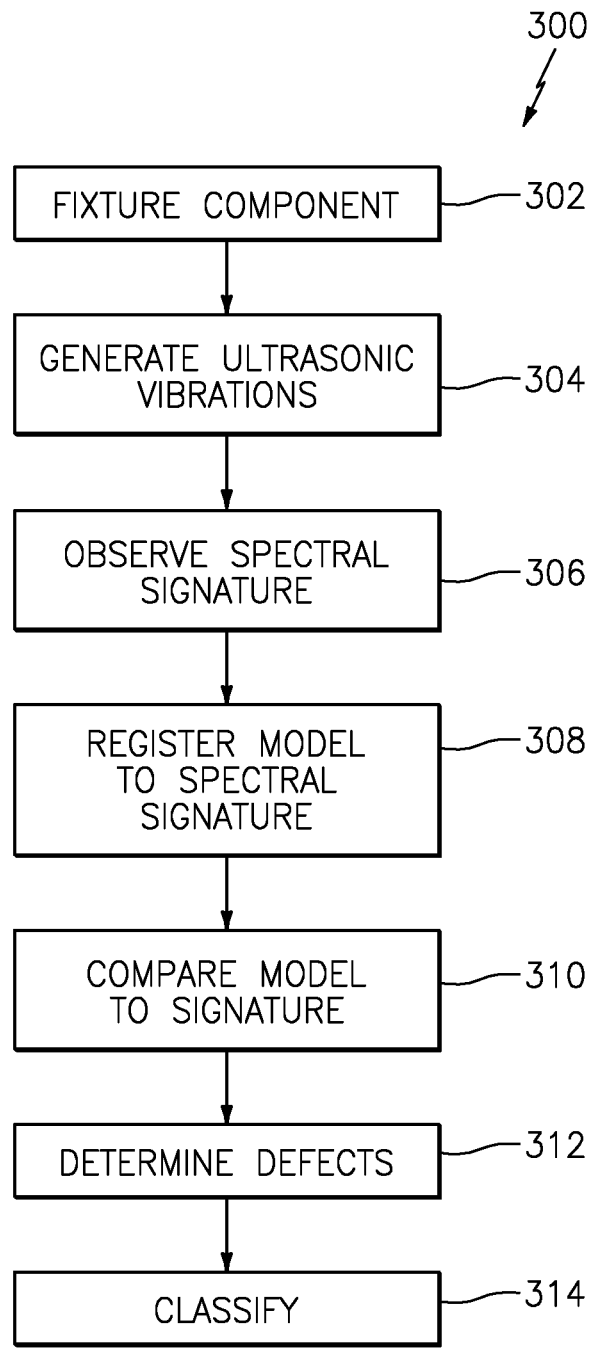
FIG. 2 is a block diagram representing a method of inspection using the nondestructive thermoacoustic imagery system.
Figure 3:
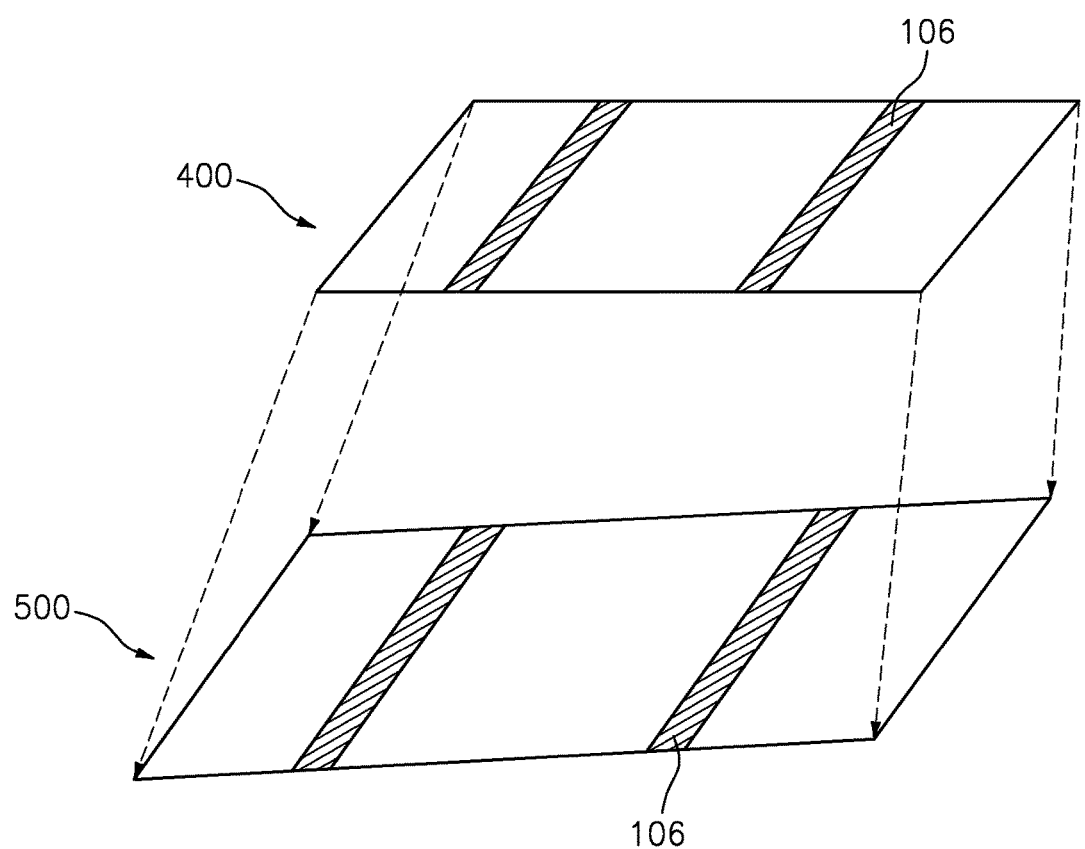
FIG. 3 is a representation of registering a model to a thermal signature of the component.

With reference to FIGS. 2 and 3, one disclosed non-limiting embodiment of a method 300 for nondestructive component inspection initially includes locating the component in the fixture 210 (step 302). The component is mounted to remove the effect of the fixture on the natural component vibrational response 210 such as with rubber pins.

The ultrasonic excitation source 220 induces elastic waves in the component 100 such that each single frequency of excitation is converted into a broad band of frequencies which are particular to resonant frequencies of the component (step 304). This vibrational energy is dissipated through conversion into heat due to friction or plastic deformation at defects in the component.

A thermal signature 500 is then observed with the thermography system 240 (step 306). The amount of heat generated depends on the frequency and position of the excitation source and the size, shape, orientation, and depth of the dissipation site, as well as the excitation power level.

A model 400 of the component 100 is stored in the component database 270 to be registered to the thermal signature 500 (step 308; FIG. 3) to provide structural information for location-dependent analysis. The model 400 stored in the component database 270 may be an as-designed model, an as-built model, a previous condition model, a model derived from the current thermal signature 500, and variations thereof for each component 100. In one nonlimiting embodiment, the model 400 may be a statistical distribution of pixel values from the thermal signature 500 as constrained by internal structure 106. Pixel values that fall outside of, for example, +/−3σ of the mean are considered anomalous. If the anomalous pixels spatially cluster relative to internal structure 106, a defect is determined to be present. The internal structure 106 is registered to thermal signature 500 via the model 400 of the component 100. The registration may make use of edges of the component 100 and the model 400 to scale, rotate, and or translate the model 400 to orient the model with respect to the component 100 to elucidate the internal structure 106 for automated reasoning about the potential location of defects. The automated reasoning may include geometry-specific algorithms for the detection of defects. The registration may include a random sample consensus (RANSAC) algorithm based on computed features where the features may include SIFT, SURF, ASIFT, other SIFT variants, Harris Corner features, SUSAN, FAST, a Phase Correlation, a Normalized Cross-Correlation, GLOH, BRIEF, CenSure/STAR, ORB, and the like.

Figure 4:
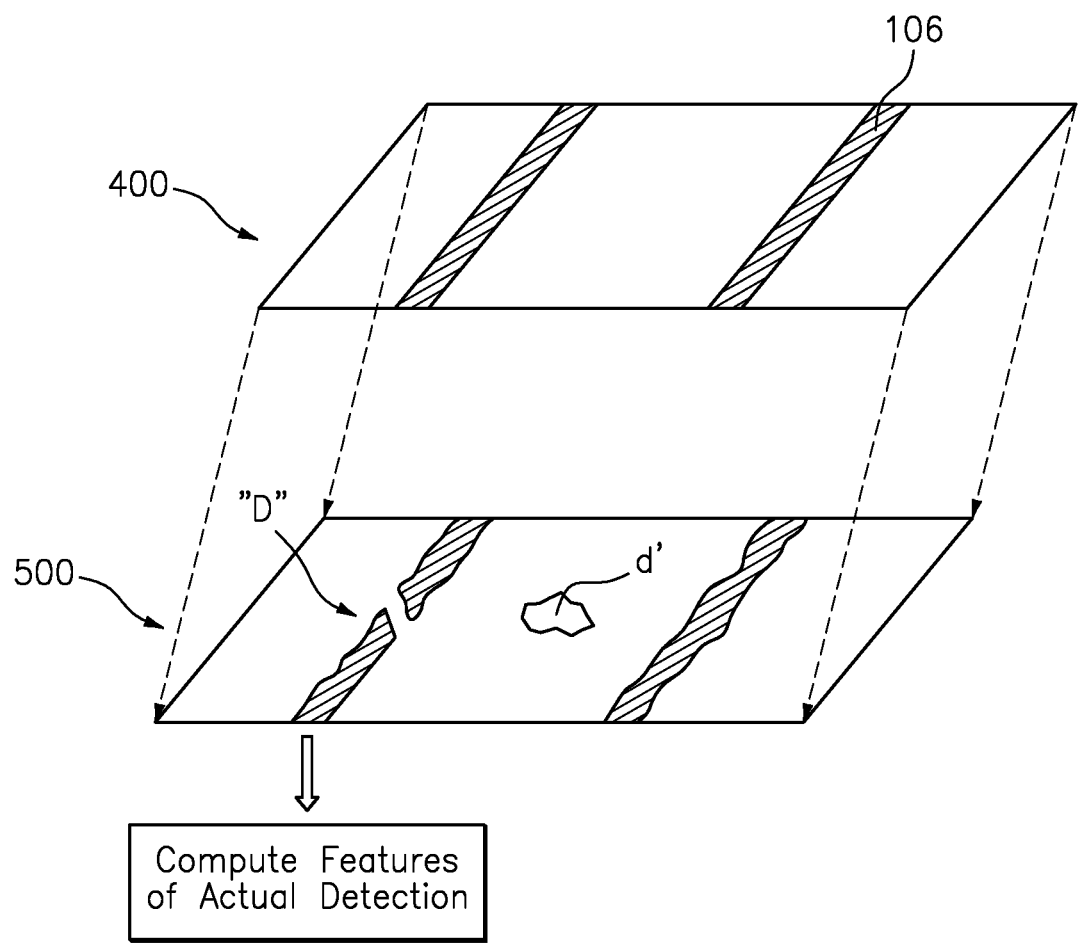
FIG. 4 is a representation of identifying a defect in a thermal signature of the component as compared to a registered model of the component.

The thermal signature 500 is then compared (step 310; FIG. 4) with the model 400 to initialize or constrain detection of defects in the thermal signature 500 to only the relevant predetermined area of the component 100 such as that defined by the internal structure 106. That is, the internal structure 106 from the model 400 is used to influence the detection of defects, particularly where the defect manifests as a 'distorted pattern' in the thermographic image 500. This may be based on, for example, initialization of an active contour shape determination, a geometric restriction for predetermined area(s) over which statistical characterization is performed as priors in a Bayesian estimation, or other technique that limits portions of the thermographic image 500 based on the model 400. For example, a defect "D," (step 312; FIG. 4) may be detected because it appears at a particular location with respect to the rigid internal structure where the identical thermal signature defect "d'" that is not adjacent the internal structure 106 may be ignored.

In embodiments, detection of defects may be performed by a geometry-dependent analysis that may include comparing the thermal signature 500 to the model 400 which delineates the internal structure 106, a pixel segmentation of the thermal signature 500 compared to the model 400, a statistical analysis of predetermined areas of the thermal signature 500, and the like.

In another embodiment, detection may be by a deep learning classifier trained from available data, such as a library of user characterized defect examples. Deep learning is the process of training or adjusting the weights of a deep neural network. In an embodiment the deep neural network is a deep convolutional neural network. Deep convolutional neural networks are trained by presenting an error map or partial error map to an input layer and a defect/no-defect label to an output layer. The training of a deep convolutional network proceeds layer-wise and does not require a label until the output layer is trained. The weights of the deep network's layers are adapted, typically by a stochastic gradient descent algorithm, to produce a correct classification. The deep learning training may use only partially labeled data, only fully labeled data, or only implicitly labeled data, or may use unlabeled data for initial or partial training with only a final training on labeled data.

In yet another embodiment, since localized heating principally occurs at the edges of the disbond, the disbond may appear as an outline or annular structure. A shape analysis may therefore also facilitate detection of the defect. The shape analysis may be based on shape descriptors such as a histogram of gradients (HoG), histogram of oriented gradients (HoOG), metrics on the diffeomorphism between the shape and a template, geodesic distances measures along the shape, shape spectrum, and the like.

Next, image recognition algorithms are utilized by the control system 250 to classify the component 100 based on the differences, e.g., defects, between the model 400 as compared to the thermal signature 500 (step 314). The component under inspection can be classified into binary (e.g. reject, accept) or multi-class categories (e.g., a score), using algorithms such as a logistics regression, nearest neighbor metrics, deep neural networks, Bayesian estimation, support vector machines, decision trees, random forests, and the like.

The nondestructive thermoacoustic imagery system 200 permits inspection of components to detect defects such as delamination or disbonding in thermographic infrared imagery and reasoning about internal shapes by registering the model and constraining the analytics based on the model. The nondestructive thermoacoustic imagery system 200 facilitates automated visual inspection that reduces cost of poor quality (COPQ) from faulty human visual inspection; reduces turn-backs from subsequent inspector disagreement; reduces dependence on increasingly scarce skilled inspectors; reduce inspection time and cost, increase inspector efficiency; and gathers machine-readable data on component condition for repair scheduling, life estimation, (re)design, and training.

The use of the terms "a", "an", "the", and similar references in the context of description (especially in the context of the following claims) are to be construed to cover both the singular and the plural, unless otherwise indicated herein or specifically contradicted by context. The modifier "about" used in connection with a quantity is inclusive of the stated value and has the meaning dictated by the context (e.g., it includes the degree of error associated with measurement of the particular quantity). All ranges disclosed herein are inclusive of the endpoints, and the endpoints are independently combinable with each other. It should be appreciated that relative positional terms such as "forward", "aft", "upper", "lower", "above", "below", and the like are with reference to normal operational attitude and should not be considered otherwise limiting.

Although the different non-limiting embodiments have specific illustrated components, the embodiments of this invention are not limited to those particular combinations. It is possible to use some of the components or features from any of the non-limiting embodiments in combination with features or components from any of the other non-limiting embodiments.

It should be appreciated that like reference numerals identify corresponding or similar elements throughout the several drawings. It should also be appreciated that although a particular component arrangement is disclosed in the illustrated embodiment, other arrangements will benefit herefrom.

Although particular step sequences are shown, described, and claimed, it should be understood that steps may be performed in any order, separated or combined unless otherwise indicated and will still benefit from the present disclosure.

The foregoing description is exemplary rather than defined by the limitations within. Various non-limiting embodiments are disclosed herein, however, one of ordinary skill in the art would recognize that various modifications and variations in light of the above teachings will fall within the scope of the appended claims. It is therefore to be understood that within the scope of the appended claims, the disclosure may be practiced other than as specifically described. For that reason, the appended claims should be studied to determine true scope and content.

What is claimed is:

1. A method for nondestructive vibrothermography inspection of a composite material component, the method comprising:
   generating ultrasonic excitations in a composite material component over a range of frequencies;
   determining a thermal signature in the composite material component from the excitations;
   comparing the thermal signature with a model of the composite material component that identifies a location of an internal structure of the composite material component; and
   classifying the composite material component based on the comparing, wherein classifying the composite material component comprises identifying a disbond area within a predetermined area that includes an internal structure.

2. The method as recited in claim 1, wherein classifying the component comprises identifying whether the component is acceptable or unacceptable.

3. The method as recited in claim 1, wherein classifying the composite material component comprises identifying the disbond area only within the predetermined area.

4. The method as recited in claim 3, wherein the predetermined area is an area that includes a rigid internal structure.

5. The method as recited in claim 4, wherein the predetermined area is adjacent the rigid internal structure and a cover.

6. The method as recited in claim 3, wherein the predetermined area is adjacent to a non-rigid internal structure and a cover.

7. The method as recited in claim 1, further comprising damping the composite material component within a fixture.

8. The method as recited in claim 1, wherein the range of frequencies comprises frequencies from 20 kHz to 2 MHz.

9. The method as recited in claim 1, wherein the thermal signature is from 0.5 to 22 µm in wavelength.

10. A method for nondestructive vibrothermography inspection of a composite material component, the method comprising:
    generating ultrasonic excitations in a component over a range of frequencies;
    determining a thermal signature in the component from the excitations;
    comparing the thermal signature with a model of the composite material component;
    identifying a defect within a predetermined area that includes an internal structure designated by the model; and
    classifying the component based on the identifying a disbond area within a predetermined area that includes an internal structure.

11. The method as recited in claim 10, wherein the predetermined area is an area that includes a rigid internal structure.

12. The method as recited in claim 11, wherein the predetermined area is adjacent the rigid internal structure and a cover.

13. The method as recited in claim 10, wherein the predetermined area is adjacent to a non-rigid internal structure and a cover.

14. The method as recited in claim 10, further comprising orienting the model with respect to the composite material component based on an edge of the model and an edge of the composite material component.

15. The method as recited in claim 10, wherein the model is at least one of an as-designed model, an as-built model, a previous condition model, and a model derived from said thermal signature.

16. A nondestructive vibrothermography inspection system to inspect a composite material component, the system comprising:
    a fixture to retain a composite material component;
    an ultrasonic excitation source directed toward the component to generate ultrasonic excitations in the composite material component over a range of frequencies;
    a thermography system directed toward the composite material component to determine a thermal signature in the composite material component from the excitations; and
    a controller operable to classify a disbond area within a predetermined area that includes an internal structure of the composite material component as a defect based on a comparison between the thermal signature of the composite material component and a model of the component that identifies a location of an internal structure of the composite material component.

17. The system as recited in claim 16, further comprising a database with the model of the composite material component that identifies the location of the internal structure of the composite material component.

18. The system as recited in claim 17, wherein the controller will only classify a portion of the composite material component as the defect if the defect is adjacent to the internal structure.

19. The system as recited in claim 16, wherein the model is at least one of an as-designed model, an as-built model, a previous condition model, and a model derived from said thermal signature.

* * * * *